(12) United States Patent
Larnard (10) Patent No.: US 6,733,442 B1
(45) Date of Patent: May 11, 2004

(54) ACCESSORY FOR SURGICAL INSTRUMENT

(75) Inventor: Donald J. Larnard, Hampton Falls, NH (US)

(73) Assignee: Seacoast Technologies, Inc., Portsmouth, NH (US)

( * ) Notice: Subject to any disclaimer, the term of this patent is extended or adjusted under 35 U.S.C. 154(b) by 0 days.

(21) Appl. No.: 10/274,940

(22) Filed: Oct. 21, 2002

(51) Int. Cl.$^7$ ................................................ A61B 1/32
(52) U.S. Cl. .......................... 600/203; 606/31; 600/459
(58) Field of Search ............. 606/27–31; 607/104–105; 600/202, 205, 459; 294/49

(56) References Cited

U.S. PATENT DOCUMENTS

| | | |
|---|---|---|
| 3,882,855 A | 5/1975 | Schulte et al. |
| 4,972,825 A | 11/1990 | Vescovo, Jr. |
| 5,007,409 A | 4/1991 | Pope |
| 5,390,734 A | 2/1995 | Voorhes et al. |
| 5,709,646 A | 1/1998 | Lange |
| 6,196,839 B1 | 3/2001 | Ross |
| 2003/0144593 A1 * | 7/2003 | Whitmore et al. .......... 600/459 |

* cited by examiner

*Primary Examiner*—Cary E. O'Connor
*Assistant Examiner*—Candice C. Melson
(74) *Attorney, Agent, or Firm*—Christopher & Weisberg, P.A.

(57) ABSTRACT

The present invention provides a surgical device for decreasing the trauma imposed on soft tissue by extended contact with a surgical device during a surgical procedure by thermally treating the tissue. To thermally treat the tissue, the surgical device can be configured to include a structure for enveloping and receiving at least a portion of the surgical device, where the structure is configured to control thermal energy transfer between the structure and the tissue.

23 Claims, 8 Drawing Sheets

ACCESSORY FOR SURGICAL INSTRUMENT

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a system and method for controlling the temperature of soft tissue through the use of a surgical device.

BACKGROUND OF THE INVENTION

Researchers and physicians have long recognized the consequences of reduction of body temperature in mammals, including induction of stupor, tissue damage, and death. Application of freezing and near freezing temperatures to selected tissue is commonly employed to preserve tissue and cell (e.g. sperm banks); and application of extreme cold (far below freezing) is effective for tissue ablation. However, localized cooling (not freezing) of tissue has generally been limited to the placement of an "ice-pack" or a "cold compress" on injured or inflamed tissue to reduce swelling and the pain associated therewith. Localized cooling of internal organs, such as the brain, has remained in large part unexplored.

For example, "brain cooling" has been induced by cooling the blood supply to the brain for certain therapies. However, as the effects of the cool blood cannot be easily localized, there is a systemic temperature reduction throughout the body that can lead to cardiac arrhythmia, immune suppression, intense shivering and coagulopathies.

Attempts have been made to localize cooling of the brain with wholly external devices, such as cooling helmets or neck collars. However, there are disadvantages associated with external cooling to affect internal tissue. For example, external methods do not provide adequate resolution for selective tissue cooling, and some of the same disadvantages that are associated with systemic cooling can occur when using external cooling devices.

During brain surgery, once a layer of tissue has been divided it must be held in place in order for the surgeon to proceed to the next level of dissection. Instruments that hold separated tissue apart can be hand-held or self-restraining retractors. In the specialized field of neurosurgery, surgeons must protect against the dangers of edema, or swelling of the brain, which may occur due to the pressure applied to the brain by the blade of a retractor. Although tissue retractors are designed to be strong enough to pull back tissue without obtrusively applying undue pressure to the operating area, edema may occur due to undue pressure applied by the retracting instrument to the brain tissue.

It has been known that post-neurosurgical edema can occur due to retraction trauma caused by a retractor in a neurosurgical procedure. For example, during an aneurysm or tumor surgery, retractors are often used to hold back lobes of brain tissue in order for the surgeon to gain access to a specific area. The pressure from the retractor is enough to traumatize the brain tissue and lead to post-surgical swelling, or edema.

It is therefore desirable to provide an improved device and method that allows for localized brain cooling while providing a layer of protection between the retractor and the brain tissue thereby preventing the possibility of trauma or edema caused by contact between the retractor blade and the brain tissue.

SUMMARY OF THE INVENTION

The present invention provides a device for decreasing the trauma imposed on soft tissue by extended contact with a retractor or retraction-like device during a surgical procedure thermally treating the tissue.

An exemplary prior art soft tissue retractor can include a deformable spatula connected to a handle element. To thermally treat the tissue, the soft tissue retractor can be configured to include a structure for enveloping and receiving at least a portion of the retractor spatula, where the structure is configured to control thermal energy transfer between the structure and the soft tissue.

For example, the structure can include a sheath dimensioned to envelope an end of the surgical instrument. A fluid conduit having a fluid inlet and a fluid outlet defining a fluid path through the fluid conduit can be attached to the exterior surface of the sheath, where the fluid conduit creates a thermal transfer region. The sheath is positioned on the spatula such that the thermal transfer region is in thermal relation with the retracted soft tissue.

To provide thermal control, the thermal transfer region is in fluid communication with a thermally-conductive fluid source such that a fluid circulation circuit is defined through the thermal transfer region.

Once the soft tissue is retracted, the thermal transfer region being in thermal communication with the soft tissue, the thermally-conductive fluid enters the thermal transfer region thermally affecting the soft-tissue. Simultaneously, thermal-conductive fluid is evacuated from the thermal transfer region. In this manner, the thermal transfer region affects a specific controlled temperature to the soft tissue.

All patents, patent applications and publications referred to or cited herein, or from which a claim for benefit of priority has been made, are incorporated by reference in their entirety to the extent they are not inconsistent with the explicit teachings of this specification, including: U.S. Pat. No. 3,882,855 to Schulte et al., U.S. Pat. No. 5,709,646 to Lange, and U.S. Pat. No. 5,007,409 to Pope.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention provides a device for decreasing the trauma imposed on soft tissue by extended contact with a retractor during a surgical procedure. As described herein, the invention includes a device and system for cooling at least a portion of a retractor.

Figure 1:
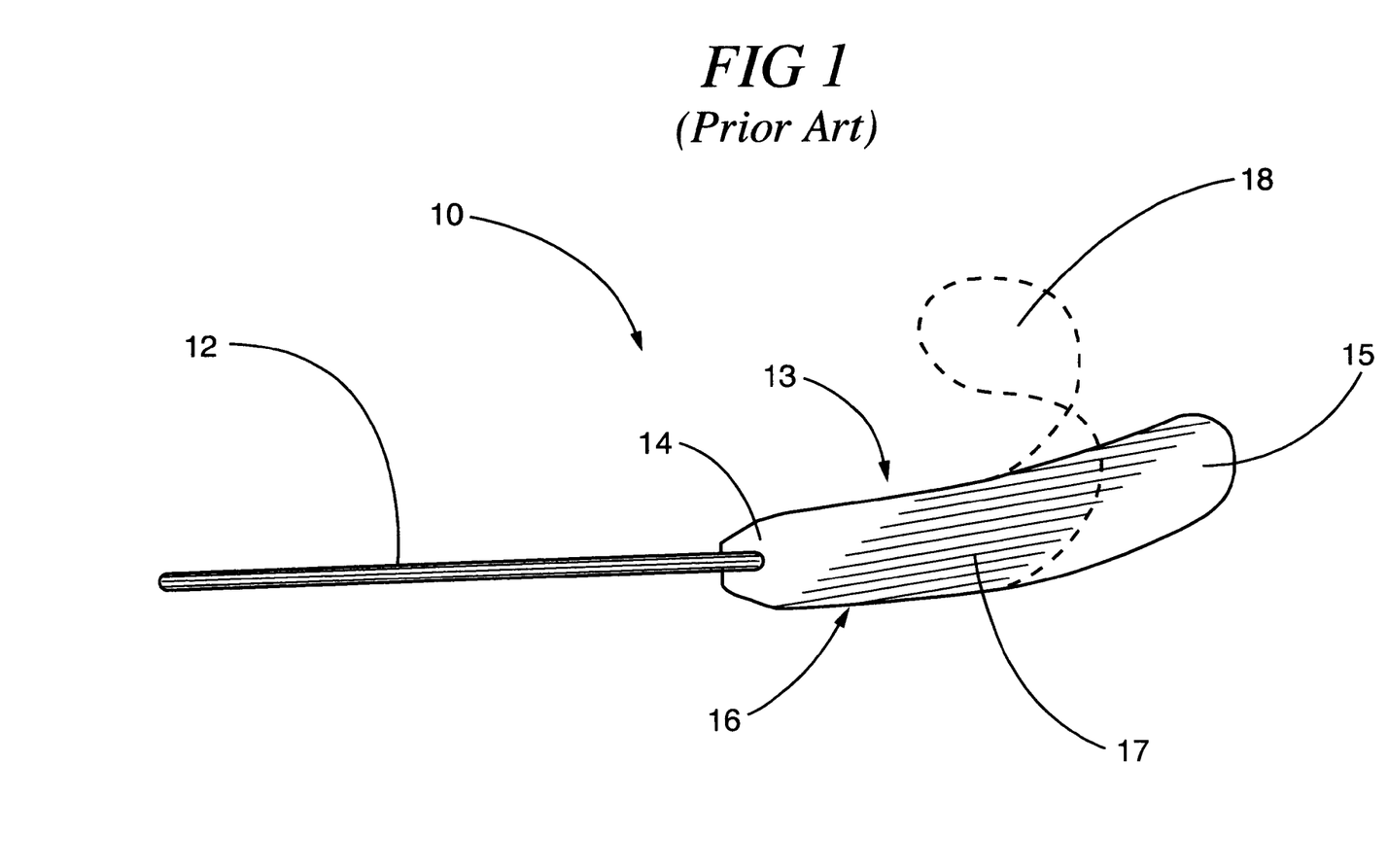
FIG. 1 is a perspective view of a prior art soft tissue retractor.

Referring now to FIG. 1, an exemplary prior art soft tissue retractor 10 is shown which can include a deformable spatula 13 having a proximal end 14, a distal end 15, a pair of opposite faces 16, 18, and a peripheral edge 17 which bounds and interconnects faces 16 and 18. The retractor 10 further includes a handle element 12, which is affixed to the proximal end 14 of the spatula 13. By "deformable" is meant an inherently shape-retaining spatula, which is sufficiently malleable that it can be deflected by application of pressure by the surgeon.

The soft tissue retractor 10 can thermally affect soft tissue by including a structure for enveloping and receiving at least a portion of the retractor 10 spatula 13, where the structure is configured to control thermal energy transfer between the structure and the soft tissue.

Figure 2:
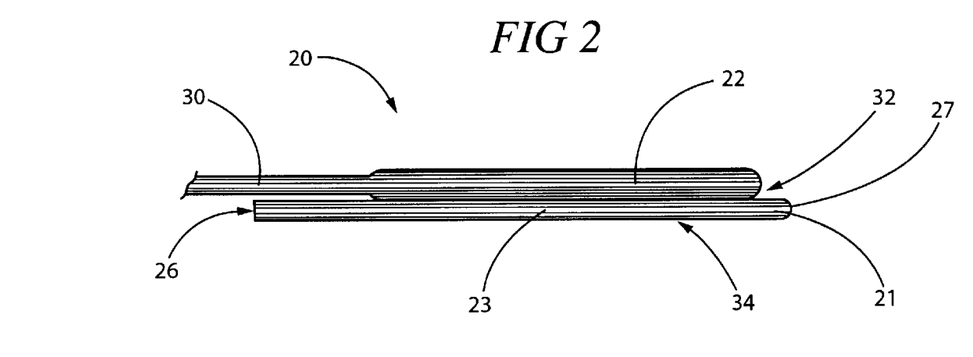
FIG. 2 is a side view of a retractor sheath of the subject invention.
Figure 3:
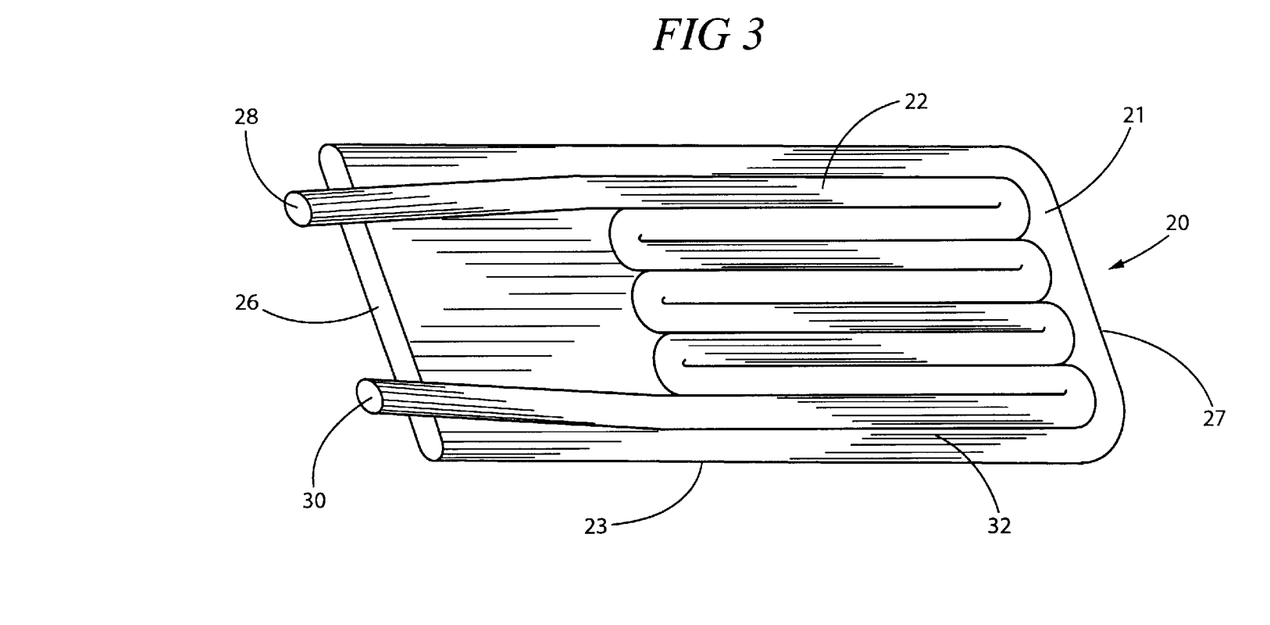
FIG. 3 is a perspective view of the retractor sheath of the subject invention.

In an embodiment of the subject invention, as shown in FIGS. 2 and 3, the thermal sheath 20 includes a sheath 21 having an open proximal end 26 and a closed distal end 27 forming a pocket shaped generally in conformity with the spatula 13, such that an upper exterior surface 32 and lower interior surface 34 of the sheath 21 are defined. The exterior surface of the sheath can be irregular, smooth, or textured. The sheath 21 can be made form an elastic or resilient material, which can conform to the shape of the spatula 13, such as, silicone polymer, soft pellethane, rubber, plastic, or mixtures thereof.

In an embodiment, a thermal transfer material is affixed to or integrated into the upper surface 32 of the sheath 21, where in an exemplary embodiment, the thermal transfer material includes a thermal conduit 22 having an fluid inlet 30 and a fluid outlet 28 substantially located at the open proximal end 26 of the sheath 21. As shown in FIG. 3, the thermal conduit 22 is folded such that a thermal transfer region 23 having longitudinal conduits is formed.

Figure 5:
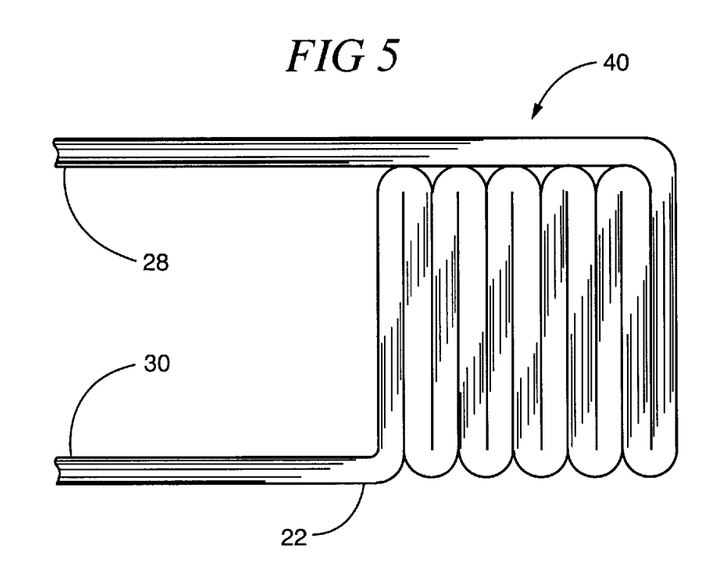
FIG. 5 is a top view of a horizontal thermal transfer region configuration of the subject invention.

In an alternative embodiment, as shown in FIG. 5, the thermal conduit 22 is folded such that a thermal transfer region 40 having horizontal conduits is formed.

Figure 6:
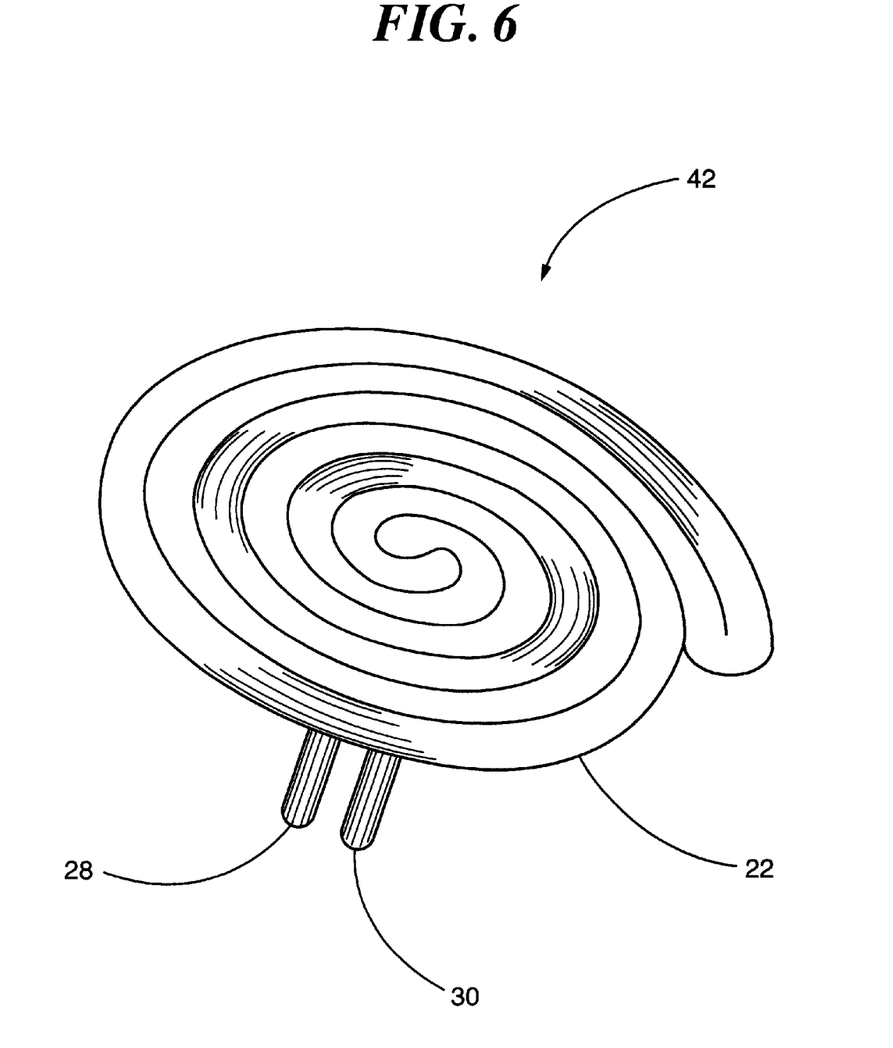
FIG. 6 is a perspective view of a spiral thermal transfer region configuration of the subject invention.

In an alternative embodiment, as shown in FIG. 6, the thermal conduit 22 is folded such that a spiral thermal transfer region 42 is formed.

The conduit 22 can be manufactured of a resilient, thermally conductive material. For example, the conduit can be manufactured from: silicone polymer, soft pellethane, rubber, plastic, or mixtures thereof.

Figure 4:
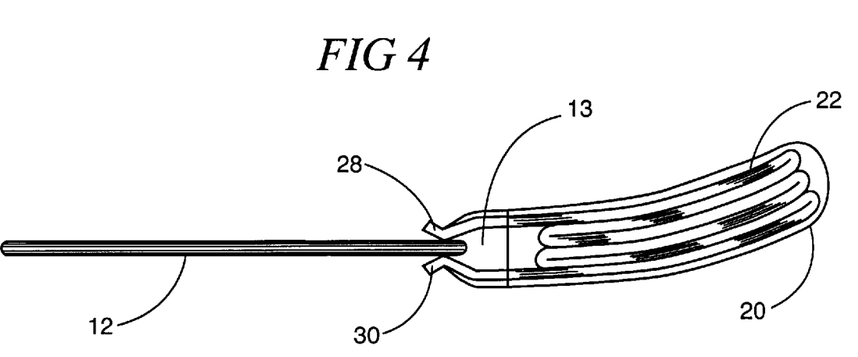
FIG. 4 is a perspective view of the retractor sheath of the subject invention installed on the spatula end of a soft tissue retractor.

In an embodiment, as shown in FIG. 4, the thermal sheath 20 is positioned over the spatula 13 by inserting the distal end 15 of the spatula 13 into the open proximal end 29 of the sheath 21. The sheath 21 is slid over spatula 13, such that the spatula distal end 15 and the sheath distal end 27 are in proximal relation, wherein the thermal transfer region 23 is positioned on the front side 16 of the spatula 13.

In an embodiment, one or more small air vent holes may be formed in the distal end 27 of the sheath near the spatula distal end 15 to facilitate the installation and removal of the sheath 21 on the spatula 13.

Figure 7:
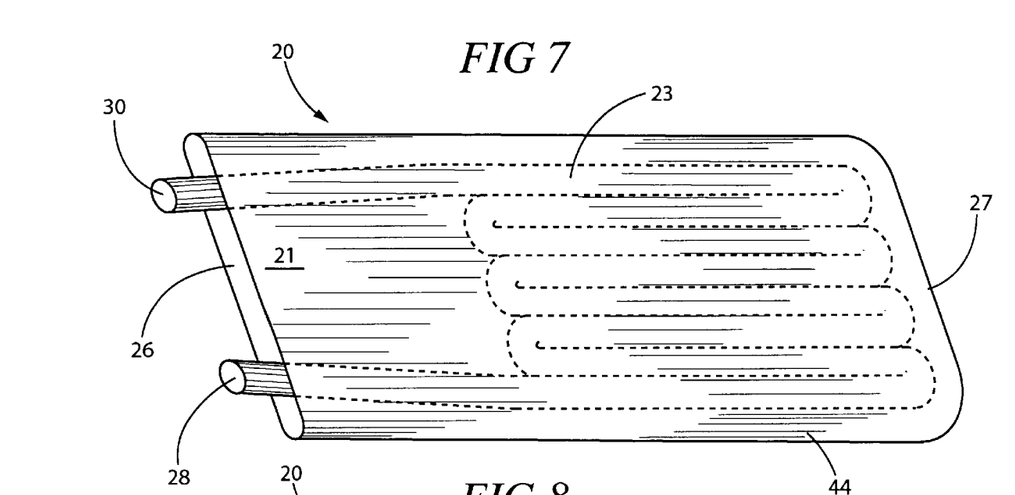
FIG. 7 is a perspective cut away view of an internal thermal transfer region of the subject invention.
Figure 8:
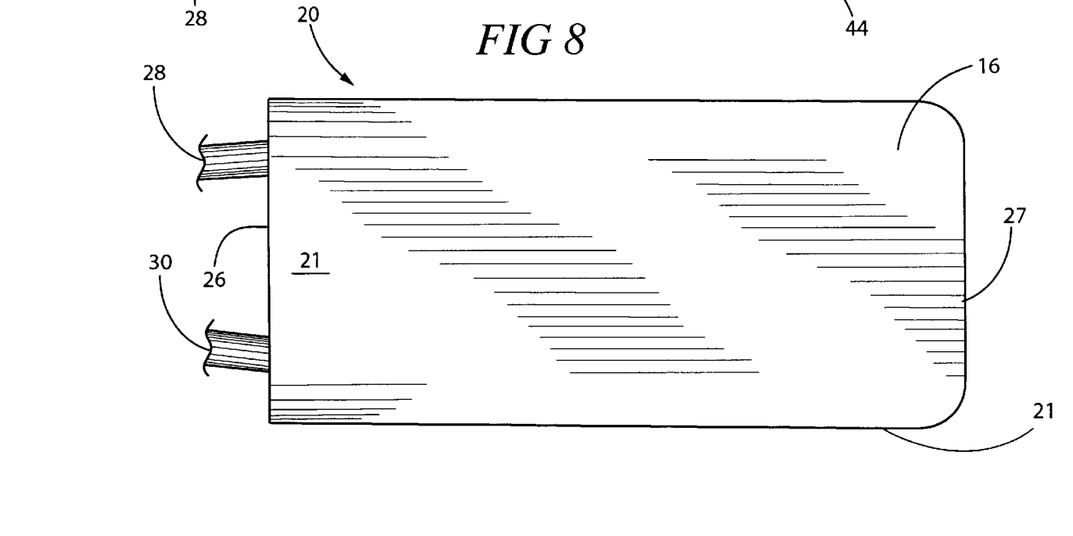
FIG. 8 is a top view of an internal thermal transfer region of the subject invention.

In an alternative embodiment, as shown in FIGS. 7 and 8 the open proximal end 26, and a closed distal end 27 of the sheath 21 further define an internal upper surface 44 and internal lower surface 46. A thermal transfer material is affixed to or integrated into the internal upper surface 44 of the sheath 21, where in an exemplary embodiment, the thermal transfer material includes a thermal conduit 22 having an fluid inlet 30 and a fluid outlet 28 substantially located at the open proximal end 26 of the sheath 21. As shown in cut-away FIG. 7, the thermal conduit 22 is folded such that a thermal transfer region 23 having longitudinal conduits is formed.

Figure 9:
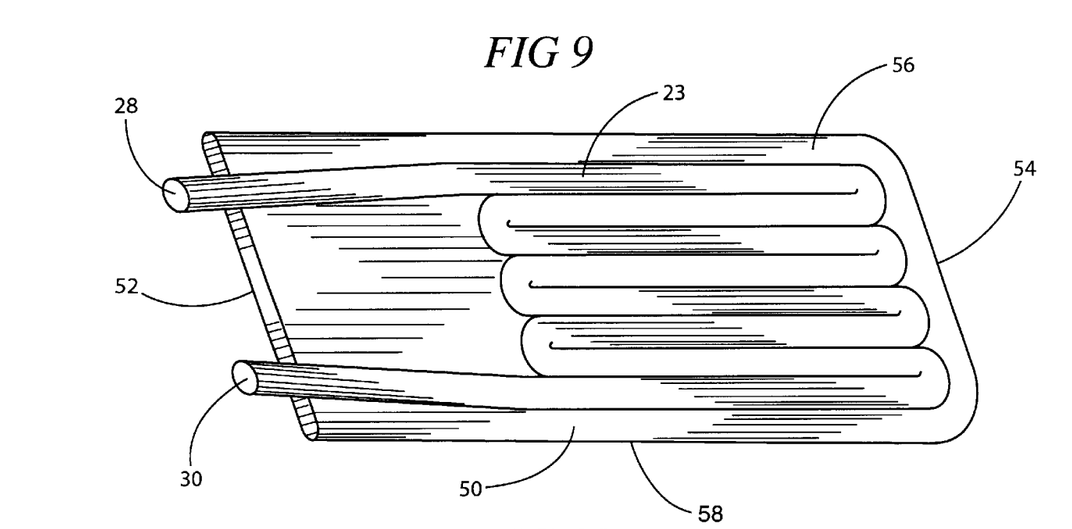
FIG. 9 is a perspective view of an adhesive patch embodiment of the subject invention.

In an alterative embodiment, as shown in FIG. 9, a thermal transfer material is affixed to an adhesive patch 50, wherein the adhesive patch includes a top surface 56, a bottom surface 58, a proximal end 52, a distal end 54, and having a shape somewhat in conformity with the spatula 13. In an exemplary embodiment, the thermal transfer material includes a thermal conduit 22 having a fluid inlet 30 and a fluid outlet 28, wherein the thermal conduit 22 is folded such that a thermal transfer region 23 having of longitudinal conduits is formed. The thermal transfer region 23 is affixed to the top surface 56 of the adhesive patch 50, such that the fluid inlet 30 and fluid outlet 28 are substantially located at the proximal end 52 of the adhesive patch 50.

Figure 10:
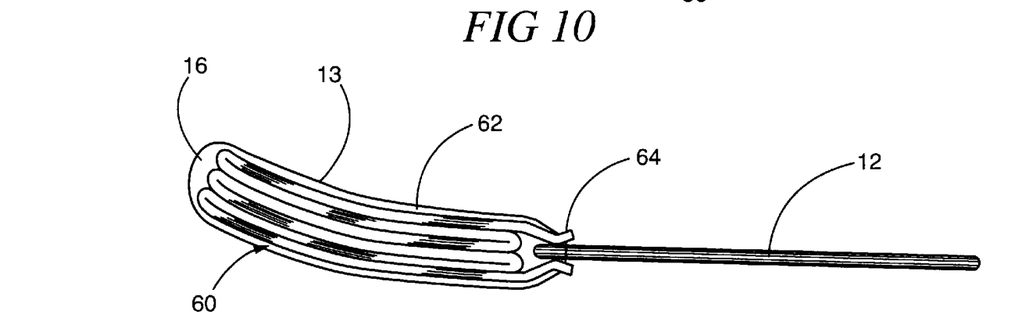
FIG. 10 is a perspective view of the thermal transfer region affixed directly to the front side of the retractors spatula.

In an alternative embodiment, as shown in FIG. 10, an exemplary soft tissue retractor 10 is shown which can include a deformable spatula 13 having a proximal end 14, a distal end 15, a pair of opposite faces 16, 18 and a peripheral edge 17 which bounds and interconnects faces 16 and 18. The retractor 10 further includes a handle element 12, which is affixed to the proximal end 14 of the spatula. Furthermore, a liquid heat sink 60 is affixed to the front side 16 of the spatula 13, where the heat sink 60 includes a serpentine fluid conduit 62 having a fluid inlet 64 and a fluid outlet 66 defining a fluid path through the heat sink 60.

In an alternative embodiment, not shown, the heat sink 60 is affixed to the backside 18 of the spatulal 3.

The heat sink 60 can be made of aluminum, copper, or other suitable metal or metal alloy, and is bonded to the spatula using techniques well know in the art.

The heat sink 60 can be manufactured of a resilient, thermally conductive material is bonded to the spatula using techniques well know in the art. For example, the heat sink can be manufactured from: silicone polymer: soft pellethane, rubber, plastic, or mixtures thereof.

Figure 11:
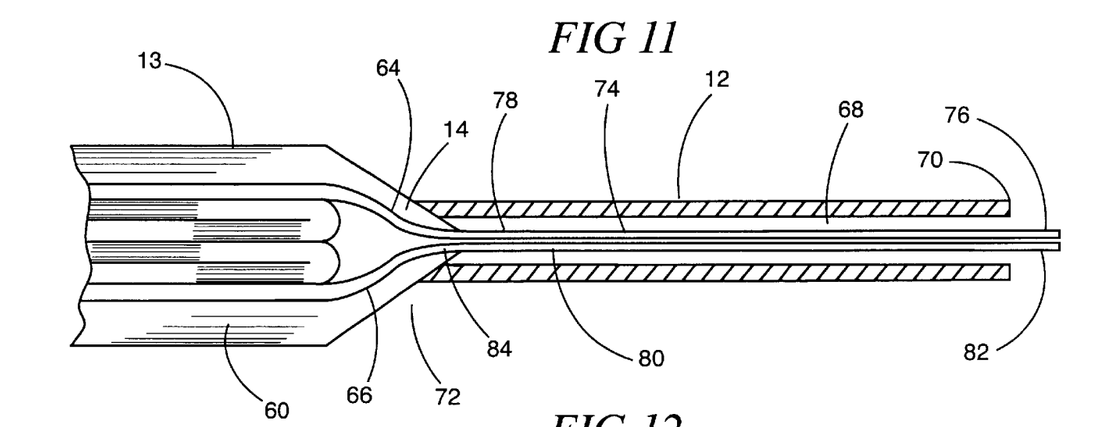
FIG. 11 is a cut away view of a hollow handle element of the subject invention.

In an alternative embodiment, as shown in FIG. 11, the handle 12 is hollow defining a handle lumen 68 having a handle proximal end 70 and a handle distal end 72, wherein the handle distal end 72 is affixed to the spatula proximal end 14. The handle 12 further includes a fluid inlet conduit 74, having a proximal end 76 and a distal end 78, and fluid outlet conduit 80, having a proximal end 82 and a distal end 84. The fluid inlet and outlet conduits 74 and 80 are positioned within the handle lumen 68, such that fluid inlet and fluid outlet conduit proximal ends 76 and 82 are located at the handle proximal end 70, and the fluid inlet and fluid outlet conduit distal ends 78 and 84 are located at the handle distal end 72. The fluid inlet 64 is connected to the fluid inlet conduit distal end 78 and the fluid outlet 66 is connected to the fluid outlet conduit distal end 84 defining a fluid path through the fluid conduits 74 and 80 and the heat sink 60.

In an alternative embodiment, the heat sink 60 is milled into either the front side 16 or backside 18 of the spatula 13, by milling a serpentine network of fluid channels and sealing off the channels with a cover plate, where the serpentine network of channels includes a fluid inlet and a fluid out defining a fluid path there through.

Figure 12:
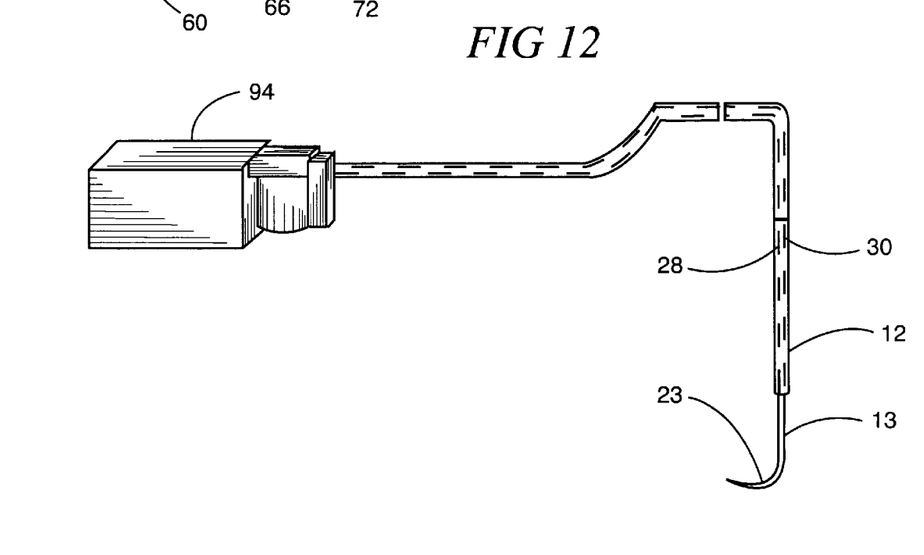
FIG. 12 is a view of an exemplary system in a bundled state.

In an exemplary system, as shown in FIG. 12, the fluid inlet 30 is in fluid communication with a thermally-conductive fluid source 94 and the fluid outlet 28 is in fluid communication with the thermally-conductive fluid source 94 such that a fluid circulation circuit is defined. In practice, once the soft tissue is retracted, the thermal transfer region 23 being in thermal communication with the soft tissue, the thermally-conductive fluid enters the thermal transfer region 23, through the fluid inlet, thermally affecting the soft-tissue. Simultaneously, the fluid outlet 28 excavates the thermally-conductive fluid from the thermal transfer region 23. In this manner, the thermal transfer region 23 affects a specific controlled temperature to the soft tissue. The thermally-conductive fluid can be saline or a refrigerant which is cooled by a thermoelectric cooler or a refrigerant fluid. Additionally, the thermal conduit 22 in the thermal transfer region 23 can be fully or partially perfusive of fluid, to thereby allow fluid to directly contact tissue for treatment purposes. In addition, a medicament or other treatment fluid can be administered in this manner.

Furthermore, the above described device can be used in any part of the body in instances where soft tissue is retracted for long duration during surgical procedures. In such instance, thermal energy may involve either chilled or heated fluid inside the thermal transfer region 23 to achieve the desired result.

Figure 13:
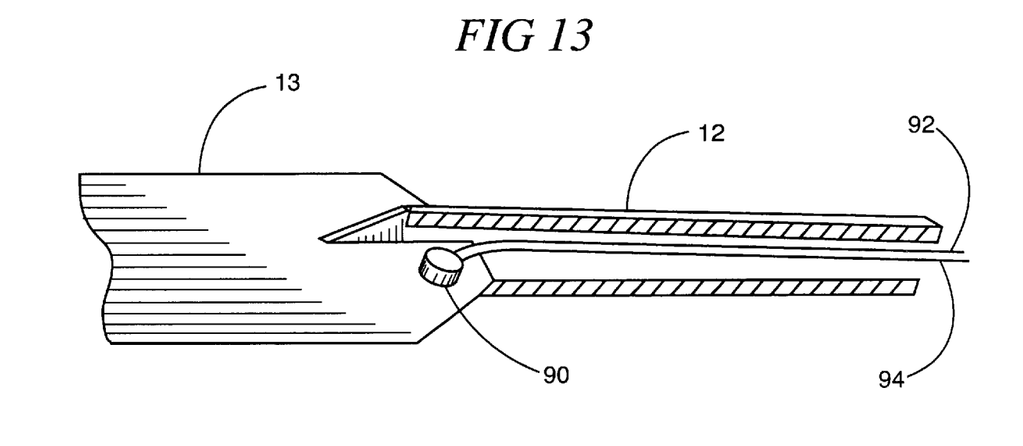
FIG. 13 is a perspective view of an embodiment of the subject invention having a thermoelectric cooling module.

In an alternative embodiment, as shown in FIG. 13, a thermoelectric module 90, sometimes called a Peltier cooler, is affixed to the spatula 13. A Peltier cooler is a semiconductor-based electronic component that functions as a small heat pump. By applying a low DC voltage to the thermoelectric module 90 through wire leads 92 and 94, heat will be moved through the thermoelectric module 90 from one side to the other. As such, one module face will therefore be cooled while the opposing face will be heated. The heat from the spatula 13 will pass from the cold face of the module to the heating face. An attached heat sink (not shown) will dissipate heat created by the thermoelectric module 90 and the heat pumped by the thermoelectric module 90.

Figure 14:
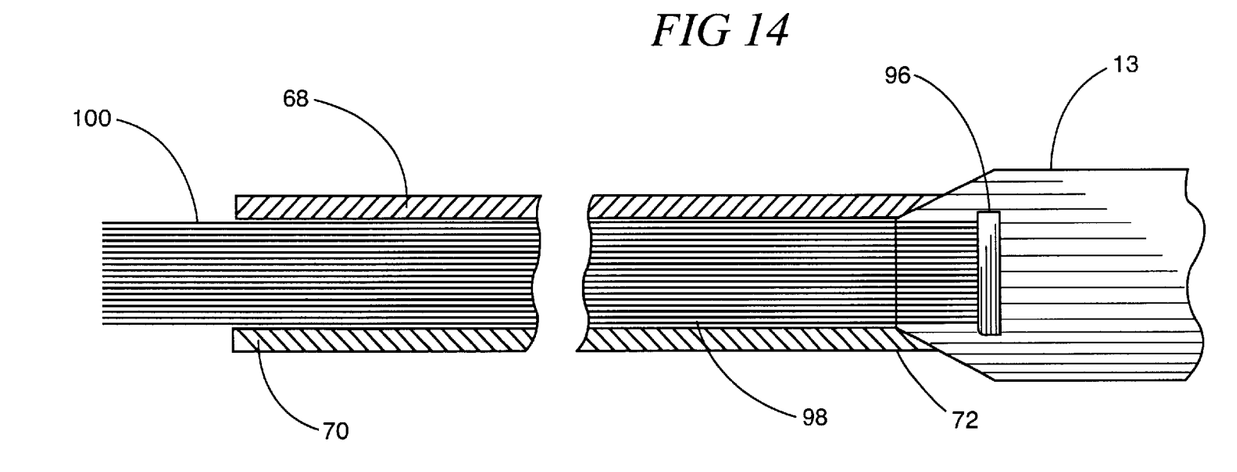
FIG. 14 is a view of perspective view of an embodiment of the subject invention comprising thermal conductive fibers.

In an alternative embodiment, as shown in FIG. 14, a heat sink 96 comprising a bundle of thermally conductive fibers 98 is affixed to the spatula 13. The thermally conductive fibers 98 extend from the heat sink 96 through the handle lumen 68 to the handle proximal end 70 to a heat dissipating end 100.

In an embodiment, the bundle of thermally conductive fibers 98 are pitch graphite fibers such as P120 or K1100 fibers produced by the Amoco Performance Products, Inc., which have an axial thermal conductivity greater than 500 W/m.degree.K. and a transverse thermal conductivity less than 100 W/m.degree.K. The transverse thermal conductivity of the portion of the fiber bundle 98 which is in contact with the spatula 13 can be increased by impregnation with a metallic substance, such as aluminum or copper in the bundle voids. The portion which makes thermal contact with the spatula 13 can have its transverse thermal conductivity further increased by tightly compressing the fibers to eliminate insulating interstitial air pockets. When the bundle of fibers 98 are in flat sheet form, the transverse thermal conductivity of the portion which makes contact with the spatula 13 can be further increased by inserting flat sheets of a more thermally conductive second material, such as copper, between the fibers 98. In alternative embodiments, the fibers are made of aluminum or copper.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A surgical device for thermally affecting soft tissue comprising a structure for enveloping and receiving at least a portion of a surgical instrument, wherein the structure is configured to control thermal energy transfer between the structure and the soft tissue, the structure comprising:

a sheath made from a resilient elastic material dimensioned to envelop an end of the surgical instrument, wherein the sheath includes an open proximal end and a closed distal end defining an interior surface and exterior surface, and a fluid conduit containing a fluid inlet and a fluid outlet defining a fluid path through the fluid conduit, wherein the fluid conduit is shaped forming a thermal transfer region, wherein the fluid conduit is affixed to the interior surface of the sheath.

2. The surgical device according to claim 1, further comprising a supply of thermo-conductive fluid in fluid communication with the structure.

3. The surgical device according to claim 1, further comprising a thermoelectric module in thermal communication with the structure.

4. The surgical device according to claim 1, wherein the structure is configured to controllably cool the soft tissue.

5. The surgical device according to claim 1, wherein the fluid conduit is shaped forming a longitudinal thermal transfer region.

6. The surgical device according to claim 1, wherein the fluid conduit is shaped forming a horizontal thermal transfer region.

7. The surgical device according to claim 1, wherein the fluid conduit is shaped forming a spiral thermal transfer region.

8. A surgical device for thermally affecting soft tissue comprising a structure for enveloping and receiving at least a portion of a surgical instrument, the structure comprising:

an adhesive patch including a top surface and a bottom surface; and a fluid conduit containing a fluid inlet and a fluid outlet defining a fluid path through the fluid conduit, wherein the fluid conduit is shaped forming a thermal transfer region, wherein the thermal conduit is affixed to the top surface of the adhesive patch, wherein the structure is configured to control thermal energy transfer between the structure and the soft tissue.

9. The surgical device according to claim 8, wherein the bottom surface of the adhesive patch comprises an adhesive coating.

10. A device for thermally affecting tissue comprising:
   a fluid conduit including a fluid inlet and a fluid outlet, wherein the fluid inlet and the fluid outlet define a fluid path through the fluid conduit, the fluid conduit being shaped to form a thermal transfer region; and
   an adhesive patch for attaching the fluid conduit to the tissue contacting surface of the medical instrument.

11. A surgical device for thermally affecting soft tissue comprising a tissue retractor having a spatula and a handle, wherein the handle is attached to the spatula and the spatula is configured to control thermal energy transfer between a tissue contact region and the soft tissue.

12. The surgical device according to claim 11, further comprising a supply of thermo-conductive fluid in fluid communication with the tissue contact region.

13. The surgical device according to claim 11, further comprising a thermoelectric module in thermal communication with the tissue contact region.

14. The surgical device according to claim 11, further comprising a bundle of thermo-conductive fiber in thermal communication with the tissue contact region.

15. The surgical device according to claim 11, wherein the tissue contact region is configured to controllably cool the soft tissue.

16. The surgical device according to claim 11, further comprising a thermal transfer operably attached to the spatula to control thermal energy transfer between the tissue contact region and the soft tissue.

17. The surgical device according to claim 16, further comprising a thermally-conductive fluid source, wherein the thermally-conductive fluid source is connected to the thermal transfer region, such that a fluid path between the thermally conductive fluid source and the thermal transfer region is defined.

18. The surgical device according to claim 16, wherein the thermal transfer region comprises a fluid conduit shaped to form the thermal transfer region, the fluid conduit comprising a fluid inlet and a fluid outlet defining a fluid path through the thermal transfer region.

19. The surgical device according to claim 16, wherein the thermal transfer region is integrated with the spatula.

20. A device for thermally affecting tissue comprising:
   a tissue retractor including a spatula and a handle, wherein the handle is attached to the spatula;
   a thermal sheath containing a sheath and a thermal transfer region, the thermal transfer region being affixed to an exterior surface of the sheath, and the thermal sheath being operable attached to the spatula, such that the thermal transfer region will be in proximal thermal relation with the tissue; and
   a thermally-conductive fluid source connected to the thermal transfer region, such that a fluid path between the thermally conductive fluid source and the thermal transfer region is defined.

21. The device for thermally affecting tissue according to claim 20, wherein the handle is hollow comprising a handle lumen having a proximal lumen end and a distal lumen end.

22. The device for thermally affecting tissue according to claim 21, wherein said handle further comprises a fluid lumen inlet conduit and a fluid lumen outlet conduit position within the handle lumen, and operatively connected to the thermal transfer region and the thermally-conductive fluid source, such that a fluid path between the thermally conductive fluid source and the thermal transfer region is defined.

23. A method of thermally treating an area of soft tissue comprising the steps of:
   providing a tissue retractor comprising a thermal transfer region;
   retracting the soft tissue such that the thermal transfer region is in thermal communication with the retracted soft tissue; and
   creating a temperature differential between the soft tissue and the thermal transfer region, such that thermal energy is transferred between the soft tissue and the thermal transfer region.

* * * * *